(12) United States Patent
Berk et al.

(10) Patent No.: US 7,841,445 B2
(45) Date of Patent: *Nov. 30, 2010

(54) DUAL-SENSOR STETHOSCOPE WITH ELECTRONIC SENSOR

(76) Inventors: Joseph Berk, 9199 Raisierstown Rd., Suite 207A, Owings Mill, MD (US) 21117; Jon L. Roberts, 529 Clear Spring Rd., Great Falls, VA (US) 22066

( * ) Notice: Subject to any disclaimer, the term of this patent is extended or adjusted under 35 U.S.C. 154(b) by 0 days.

This patent is subject to a terminal disclaimer.

(21) Appl. No.: 12/419,415

(22) Filed: Apr. 7, 2009

(65) Prior Publication Data

US 2009/0232323 A1    Sep. 17, 2009

Related U.S. Application Data

(63) Continuation-in-part of application No. 11/937,929, filed on Nov. 9, 2007, now Pat. No. 7,516,814.

(51) Int. Cl.
 A61B 7/02 (2006.01)
 A61B 7/00 (2006.01)
 A61B 5/02 (2006.01)
(52) U.S. Cl. .................... 181/131; 381/67; 600/528
(58) Field of Classification Search ............. 181/131, 181/137, 125; 381/67; 600/528
 See application file for complete search history.

(56) References Cited

U.S. PATENT DOCUMENTS

| | | | | | |
|---|---|---|---|---|---|
| 224,199 | A | * | 2/1880 | Mayer | 181/125 |
| 939,349 | A | * | 11/1909 | Taylor | 181/125 |
| 1,569,292 | A | * | 1/1926 | Mason | 181/125 |
| 1,671,936 | A | * | 5/1928 | Rieger | 181/137 |
| 1,708,398 | A | * | 4/1929 | Pilling | 181/131 |
| 1,733,718 | A | * | 10/1929 | Blondel | 181/125 |
| 1,811,558 | A | * | 6/1931 | Porter | 181/131 |
| 1,847,607 | A | * | 3/1932 | Hardt | 181/131 |
| 1,853,951 | A | * | 4/1932 | Zala | 181/131 |
| 2,209,164 | A | * | 7/1940 | Kerr | 181/131 |
| 2,230,794 | A | * | 2/1941 | Danischewsky | 181/131 |
| 2,515,471 | A | * | 7/1950 | Ratzan | 181/131 |
| 2,722,989 | A | * | 11/1955 | Tynan | 181/131 |
| 2,902,108 | A | * | 9/1959 | Briskier | 181/137 |
| 3,124,211 | A | * | 3/1964 | Cefaly | 181/131 |

(Continued)

FOREIGN PATENT DOCUMENTS

DE    3218003 A1 * 11/1983

(Continued)

*Primary Examiner*—Edgardo San Martin
(74) *Attorney, Agent, or Firm*—The Marbury Law Group PLLC

(57) ABSTRACT

A dual-sensor stethoscope, or retrofit device for a stethoscope, promotes anti-sepsis and stereoscopy through use of a substantially rigid, generally T-shaped tube for support of dual stethoscope sensors, wherein at least one sensor is electronic. Each sensor may be rotated away from a body independently for use of a single head or rotated into the same general plane for dual-head stereoscopy. A clinician can create a spatial, three-dimensional (3D) antiseptic barrier and avoid the need to carry multiple stethoscopes. During stereoscopy, the use of a common tube or earphones allows the transmission of sound with constructive interference of sound waves. The substantially rigid, generally T-shaped support tube allows a clinician to auscultate with one hand and monitor two locations without transference of pathogens.

20 Claims, 10 Drawing Sheets

U.S. PATENT DOCUMENTS

| | | | | |
|---|---|---|---|---|
| 3,144,091 | A * | 8/1964 | Bodenger | 181/137 |
| 3,247,324 | A * | 4/1966 | Cefaly et al. | 381/67 |
| 3,630,308 | A * | 12/1971 | Ravin | 181/131 |
| 3,767,003 | A * | 10/1973 | Shacklock | 181/137 |
| 4,064,965 | A * | 12/1977 | Brown | 181/131 |
| 4,200,169 | A * | 4/1980 | MacDonald et al. | 181/131 |
| 4,438,772 | A * | 3/1984 | Slavin | 600/528 |
| 4,528,690 | A * | 7/1985 | Sedgwick | 381/67 |
| 4,618,986 | A * | 10/1986 | Hower | 381/67 |
| 4,706,777 | A * | 11/1987 | Baumberg | 181/131 |
| 4,783,813 | A * | 11/1988 | Kempka | 381/67 |
| 4,821,327 | A * | 4/1989 | Furugard et al. | 381/67 |
| 4,997,055 | A * | 3/1991 | Grady | 181/131 |
| 5,347,583 | A * | 9/1994 | Dieken et al. | 381/67 |
| 5,548,651 | A * | 8/1996 | Long | 381/67 |
| 5,557,681 | A * | 9/1996 | Thomasson | 381/67 |
| 5,638,453 | A * | 6/1997 | McLaughlin | 381/67 |
| 5,650,598 | A * | 7/1997 | Abelson | 181/131 |
| 5,717,769 | A * | 2/1998 | Williams | 381/67 |
| 5,852,263 | A * | 12/1998 | Dieken | 181/131 |
| 5,910,992 | A * | 6/1999 | Ho | 381/67 |
| 5,931,792 | A * | 8/1999 | Packard et al. | 600/528 |
| 5,932,849 | A * | 8/1999 | Dieken | 181/131 |
| 5,959,261 | A * | 9/1999 | Abelson | 181/131 |
| 6,726,635 | B1 * | 4/2004 | LaSala | 600/528 |
| 7,516,814 | B1 * | 4/2009 | Berk et al. | 181/131 |
| 2004/0220487 | A1 * | 11/2004 | Vyshedskiy et al. | 600/513 |
| 2004/0226771 | A1 * | 11/2004 | Werblud | 181/131 |
| 2008/0232604 | A1 * | 9/2008 | Dufresne et al. | 381/67 |

FOREIGN PATENT DOCUMENTS

DE          3329809 A1 * 2/1985

* cited by examiner

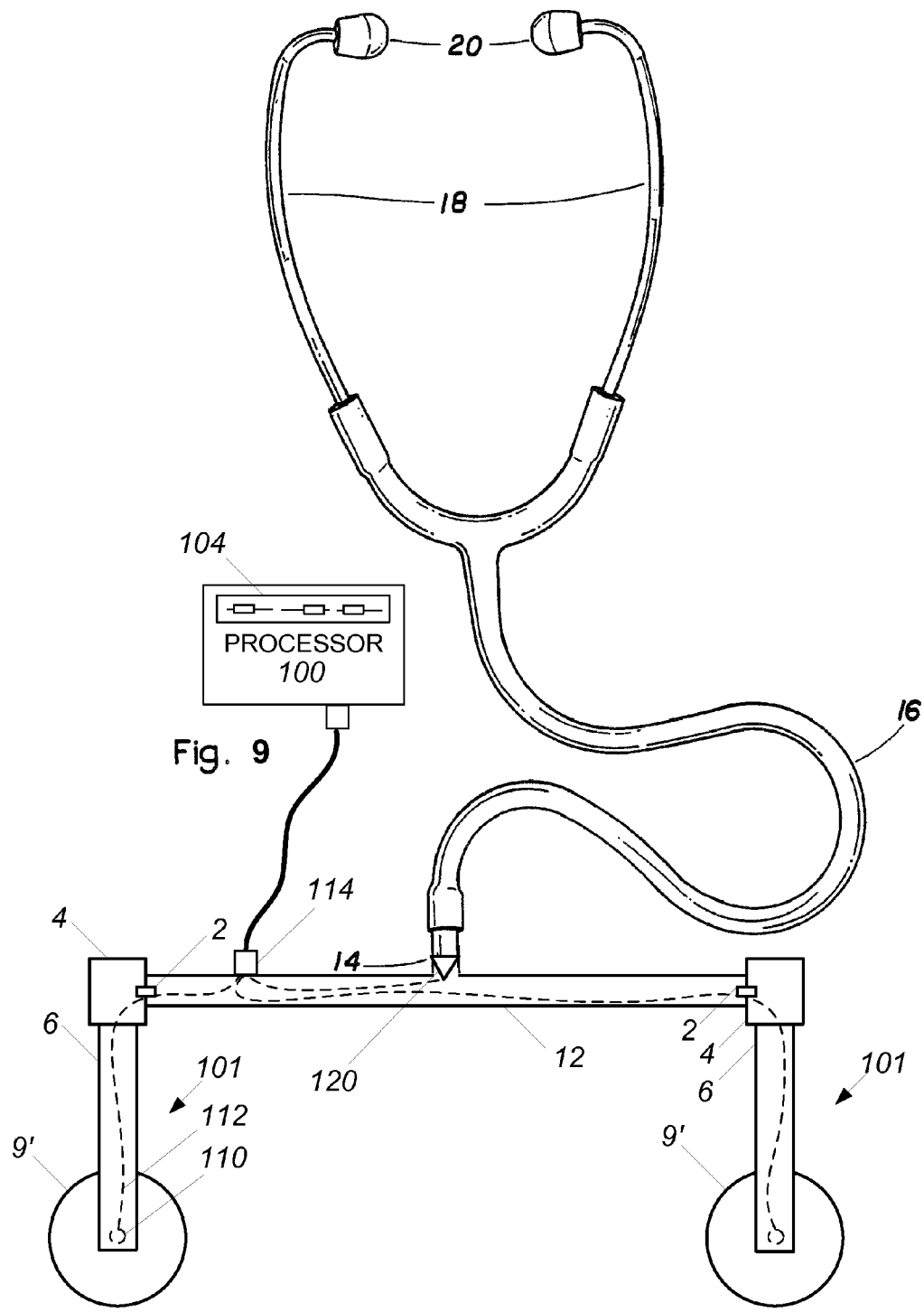

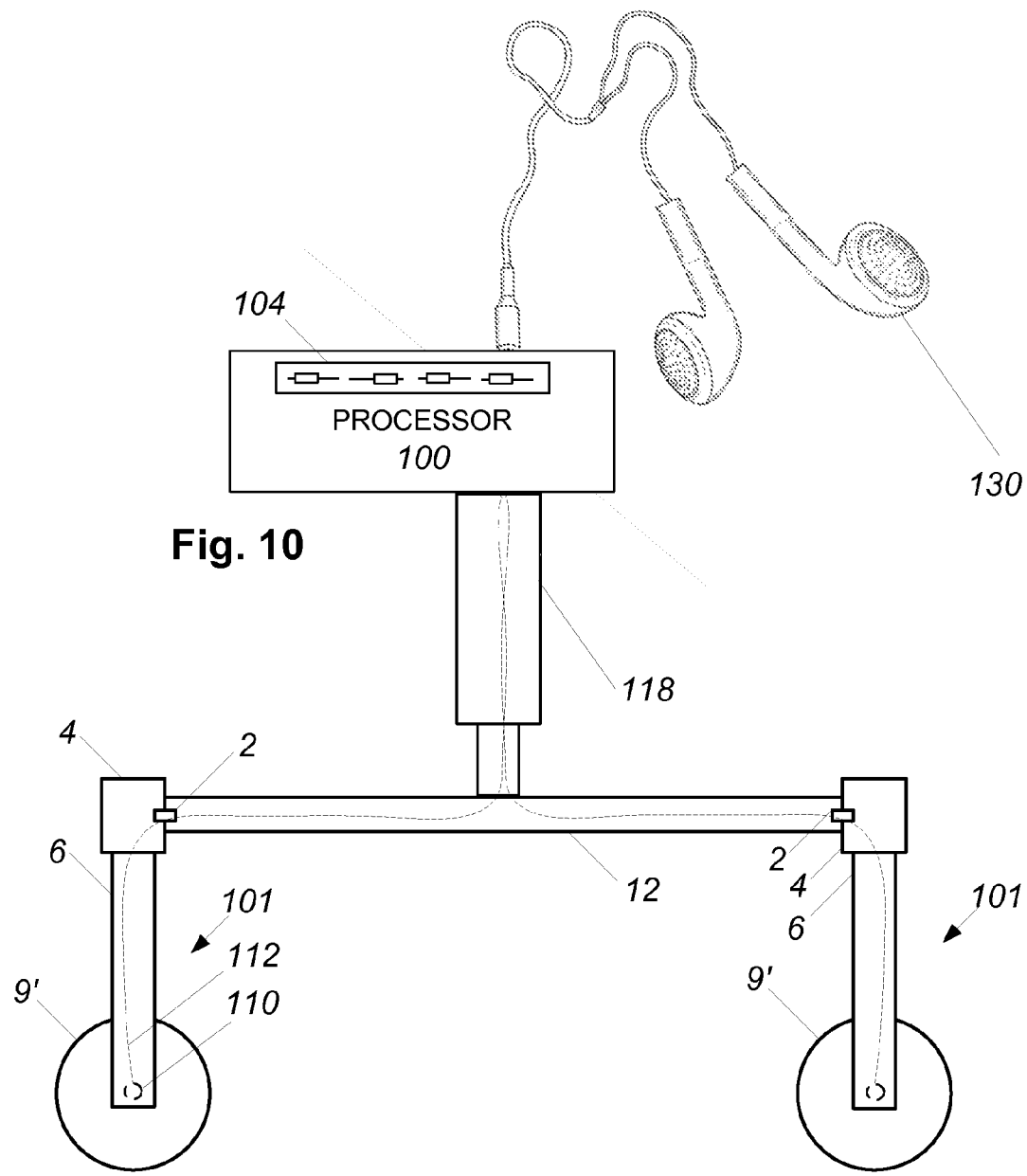

DUAL-SENSOR STETHOSCOPE WITH ELECTRONIC SENSOR

RELATED APPLICATIONS

This application is a continuation-in-part of application Ser. No. 11/937,929, filed Nov. 9, 2007, now U.S. Pat. No. 7,516,814, issued Apr. 14, 2009, which is hereby incorporated by reference for all purposes.

BACKGROUND

The embodiments disclosed herein are drawn generally to a dual-sensor stethoscope that promotes anti-sepsis, stereoscopy, and advanced sound processing. In particular, a stethoscope with dual-sensors on a T-shaped support is disclosed, wherein at least one sensor is electronic.

Existing stethoscopes are currently utilized to auscultate or listen to physiologic sounds within the body. Auscultation with existing stethoscopes is currently performed by intermittently applying a stethoscope to the body surface through which the clinician hears various sounds. Intermittent auscultation may be thought of as a relatively benign procedure. However, several disadvantages and hazards are associated with the use of existing stethoscopes. First, patients undergoing surgery may have the sterile field invaded thereby risking infection in order for the clinician to auscultate the chest. To avoid cross-contamination between patients, many clinicians are forced to carry multiple stethoscopes. Additionally, even when a sterile stethoscope is used, it can transfer pathogens from a first location on a patient's body to a second location during typical auscultation. Furthermore, even in non-surgical environments, transmission of the cold virus is primarily through touch. A clinician's hand can touch the head of a stethoscope, which then touches a patient and vice versa so as to spread the virus. These issues exist whether the stethoscope uses an acoustic (mechanical) sensor or an electronic sensor.

Another disadvantage of known stethoscopes is that patients are frequently awakened and disturbed so that the clinician may apply a cold stethoscope to the patient's chest to monitor vital signs. Studies have shown serious developmental abnormalities in newborn infants who are frequently disturbed to auscultate heart and lung sounds with known stethoscopes. Another disadvantage of existing stethoscopes is that the quality of sound wave transmission is dependent upon an airtight seal between the stethoscope and the skin, typically requiring the clinician to touch, and possibly contaminate, the sensor. In the absence of an airtight seal, background noise is inadvertently detected and physiologic sound transmission is impaired. Finally, another disadvantage of existing stethoscopes is that most are not capable of generating positive or constructive interference, filtering certain frequencies, or providing other processing of physiologic sound waves.

BRIEF SUMMARY

The disclosed embodiments provide a dual-sensor stethoscope that promotes antisepsis, stereoscopy, and advanced audio processing through use of a substantially rigid, generally T-shaped tube for support of dual stethoscope sensors, wherein at least one sensor is electronic. Each each sensor may be rotated away from a body independently for use of a single head or rotated into the same general plane for dual-sensor use, such as for stereoscopy. In this manner, a clinician can create a spatial, three-dimensional (3D) anti-septic barrier and avoid the need to carry multiple stethoscopes. When two sensors are used for stereoscopy, the use of at least one electronic sensor allows for advanced processing of sound waves. In all cases, the substantially rigid, generally T-shaped support tube allows a clinician to auscultate with one hand. The rigid support tube also allows a clinician to obtain a good seal during auscultation without the need to touch any portion of the stethoscope sensor(s), thus preventing any possible contamination of the sensor from the clinician's hand.

The support tube, and even the sensors (mechanical or electronic), can optionally be disposable to further promote anti-sepsis. The support tube, in various embodiments, can be designed to be retrofitted to any standard stethoscope and use standard stethoscope heads when only a single electronic sensor is employed. Use of a standard stethoscope heads allows the device to take advantage of the ordinary ability of a mechanical stethoscope head with a bell and diaphragm to be "turned off" by rotation of the head. The structure of the support tube can also provide a means to close the sound transmission path or disconnect an electronic sensor when a sensor is rotated away from a patient.

In one embodiment, a stethoscope incorporates a rigid, generally T-shaped support tube for connecting a common sound transporting tube with two rotatable sensor-supporting tubes, with at least one electronic sensor.

In another embodiment, a rigid, generally T-shaped support tube is disclosed for connection to a common sound transporting tube of a stethoscope at a first end and two stethoscope heads at a second end of a pair of movable rotatable sensor-supporting tubes, with at least one electronic sensor.

In a further embodiment, a rigid, generally T-shaped support tube is disclosed for retrofitting to a stethoscope for connecting a common sound transporting tube with two rotatable sensor-supporting tubes, with at least one electronic sensor.

In another embodiment, the rigid, generally T-shaped support tube for retrofitting to a stethoscope for connecting a common sound transporting tube with two rotatable head-supporting tubes is formed of disposable material.

In another embodiment, rotatable head-supporting tubes on the rigid, generally T-shaped support tube for a stethoscope include detents or locking means for positioning the rotatable head-supporting tubes in predetermined positions.

In yet another embodiment, the rigid, generally T-shaped support tube is adapted for use with pediatric stethoscopes and sensors.

In a further embodiment, the rigid, generally T-shaped support tube is disposable and includes integral disposable sensors, wherein at least one sensor is electronic.

BRIEF DESCRIPTION OF THE DRAWINGS

FIG. 9 illustrates an embodiment with a pair of electronic sensors.

FIG. 10 illustrates another embodiment with a pair of electronic sensors.

DETAILED DESCRIPTION

As used herein, the terms head, sensor or sensor head refer to a stethoscope sensor and its attachment means that may comprise: a mechanical diaphragm, bell, or combination of the two, or an electronic stethoscope sensor incorporating a microphone; the terms rotate and rotatable refer to movement about an actual or virtual pivot point; and the terms tube and tubular refer to any hollow structure for conduction of sound waves or any structure for routing of electronic wiring and is not limited to circular cross-sections.

Figure 1:
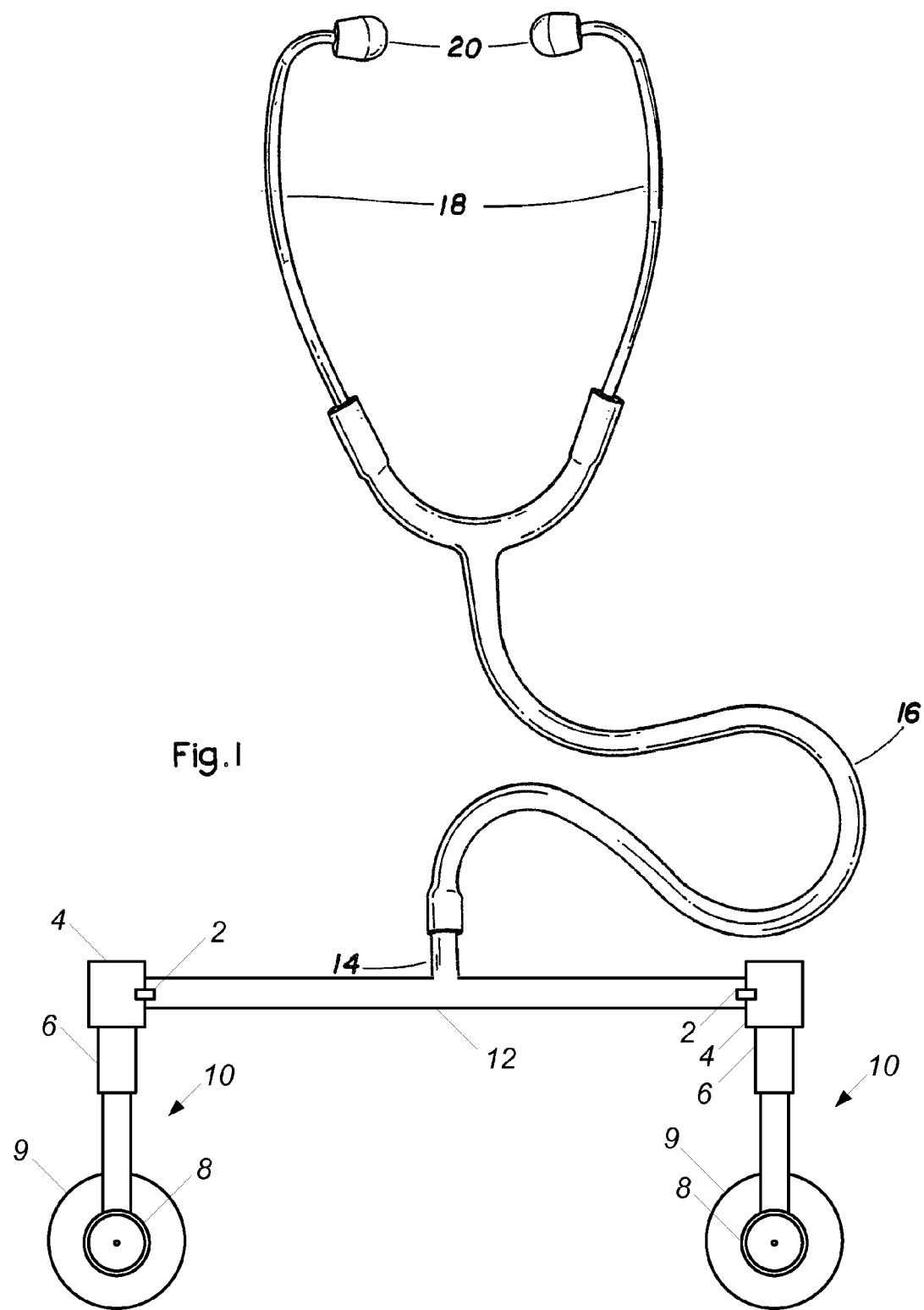
FIG. 1 illustrates an embodiment of a stethoscope in a stereoscopic configuration.
Figure 3:
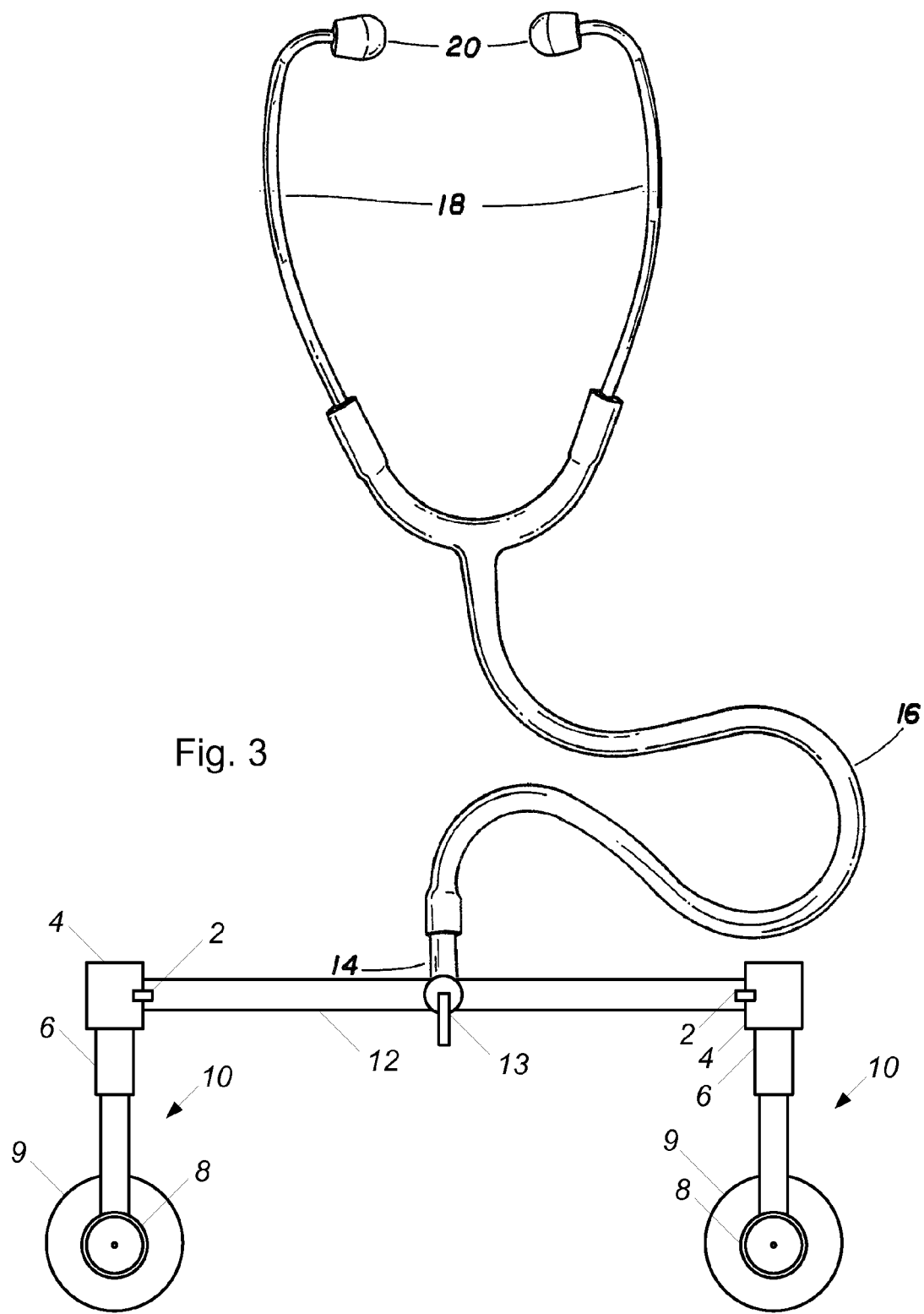
FIG. 3 illustrates an embodiment utilizing a three-way stopcock.

As illustrated in FIG. 1, an embodiment of a stethoscope includes conventional eartips 20 and earpieces 18 connected to common sound conduction tube 16. In place of a conventional stethoscope head at the end of the tube 16, a substantially rigid structure is used to mount two sensors 10 to the stethoscope. In use, a clinician can handle the rigid structure to position the sensors 10 and thus avoid contamination of the sensors 10 from any pathogens that may be on the clinician's hands. In the illustrated configuration of FIG. 1, the stethoscope is configured in a position for stereoscopy wherein the stethoscope sensors 10 will transmit sound through common sound conduction tube 16, which results in constructive interference of sound waves. In an alternate embodiment, as illustrated in FIG. 3, a three-way stopcock 13 can be used to select between stereoscopic sensing and sensing from either one or the other sensor head 10. In this manner, a clinician can selectively listen to two locations on a patient without transferring any pathogens between the two locations.

A generally T-shaped support tube includes a first tubular element 14 sized for connecting to common sound conduction tube 16. When used with conventional stethoscopes, the element 14 will be a tube having the same dimensions as the connection tube of a conventional sensor head. Similarly, when used with pediatric stethoscopes, the element 14 will be a tube having the same dimensions as the connection tube of a pediatric sensor head or can alternately include an adapter element (not shown) to allow connection to a pediatric stethoscope.

The T-shaped support tube further includes tube 12 that communicates with element 14 in a central portion and with two rotatable head-supporting tubes 6 at first and second spaced ends of tube 12. Head-supporting tubes 6, when used with conventional stethoscope sensors, are dimensioned to allow insertion and connection of conventional sensor heads 10 with bells 8 and/or diaphragms 9, whether regular and pediatric. Tubes 6 are rotatably attached to tube 12 with rotatable couplings 4 that can be integral or separate from tubes 6. The rotatable coupling 4 preferably includes or cooperates with a detent or locking means 2 so as to form a substantially rigid support for the sensors 10 that the clinician can grasp and use for obtaining the desired seal or contact of the sensor 10 against the patient.

Figure 7:
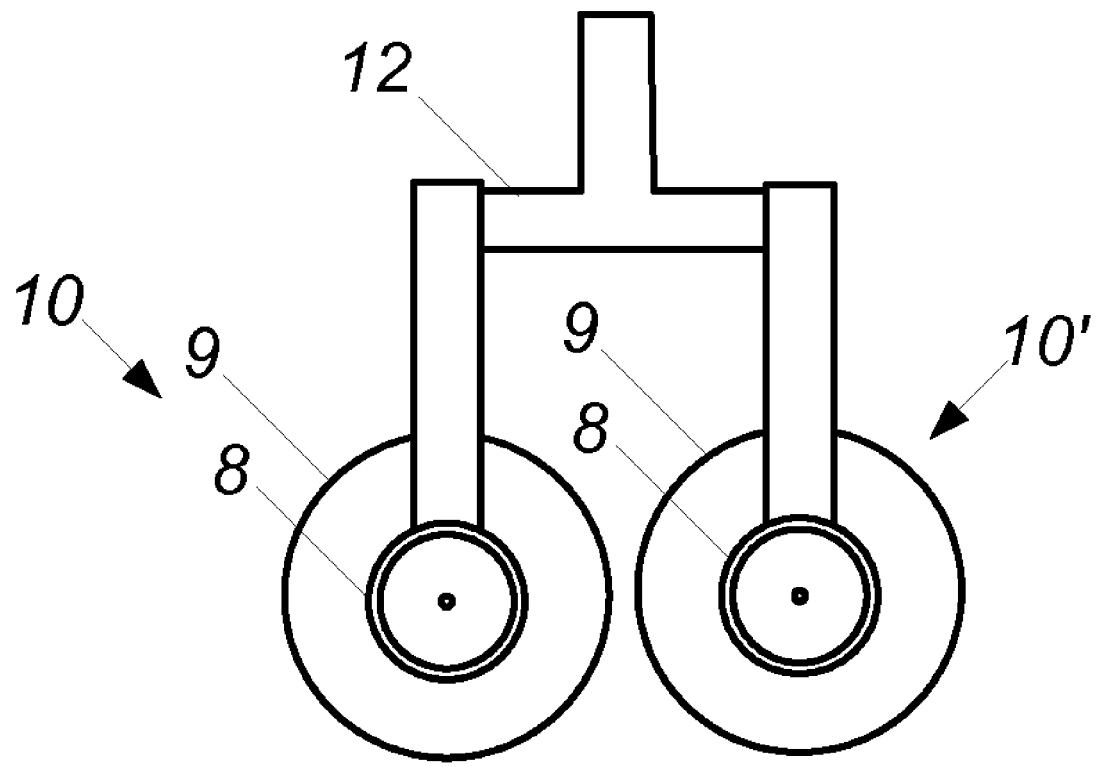
FIG. 7 illustrates an embodiment for single-hand use.

Although the length of tube 12 is illustrated to show a clear distance between the sensor heads 10, in some embodiments it may be preferable to minimize the length of tube 12 (e.g., only slightly longer than the diameter of each sensor head) in order to allow a clinician to manipulate both sensor heads 10 with a single hand, as illustrated in FIG. 7. Additionally, although tubes 6 are illustrated as being identical, the tubes 6 can also have different lengths or have different diameters to allow the use of variously-sized sensors (e.g., a full-sized sensor and a pediatric sensor) on the same stethoscope. Further, an embodiment may comprise only elements 2, 4, 6, 8, 9, 10, 12, and 14 as a separate unit to retro-fit to existing stethoscopes.

Figure 2:
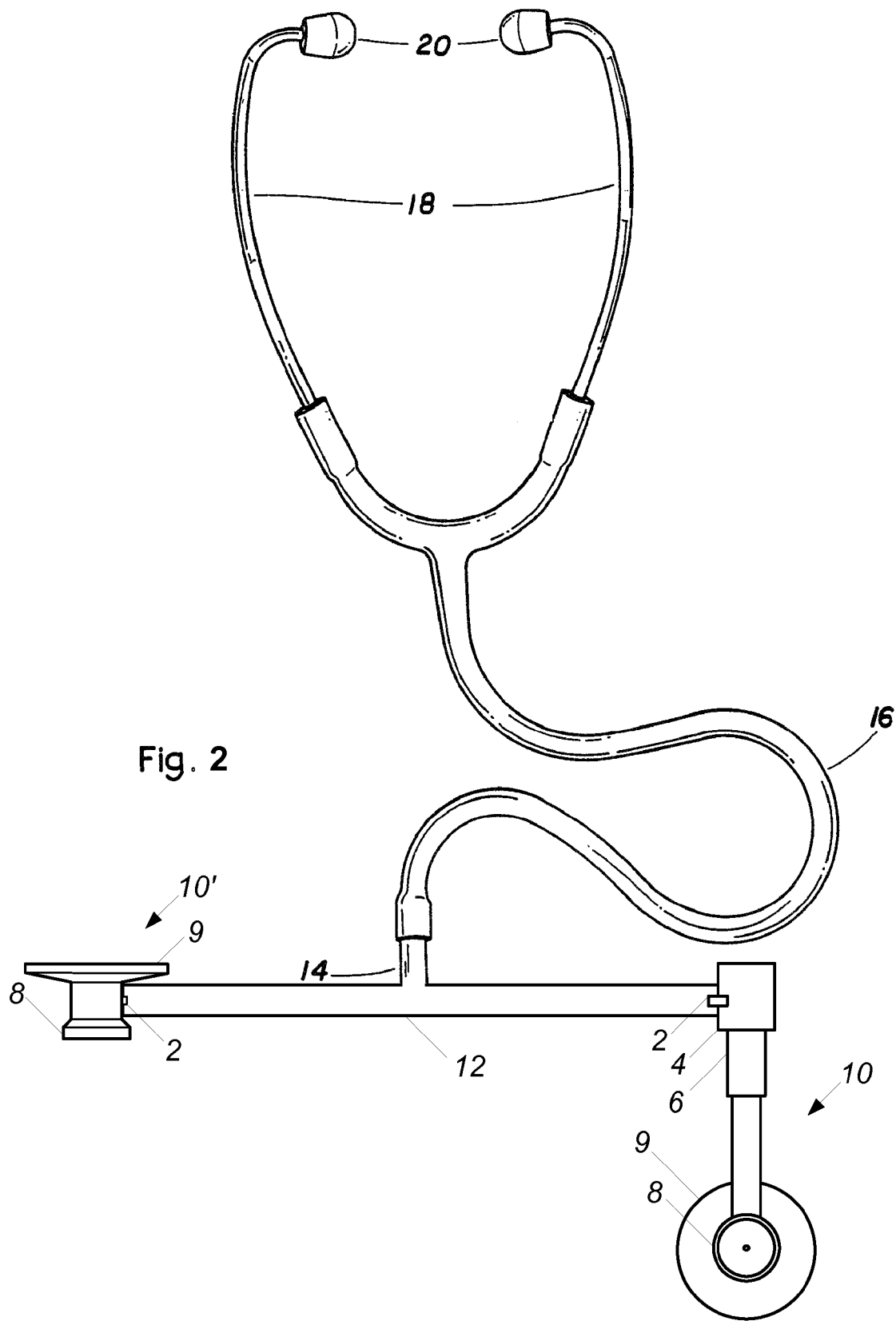
FIG. 2 illustrates an embodiment with one head of the stethoscope rotated away to provide a spatial (3D) anti-septic barrier.

As illustrated in FIG. 2, which uses identical reference numbers for identical elements, either sensor head 10' may be rotated into another position to create a spatial, 3D anti-septic barrier. Additionally, conventional sensor heads 10' can be "turned off" in the conventional manner by rotation of the diaphragm/bell unit, as illustrated in FIG. 2. In certain embodiments, such as low-cost or disposable variations with only a single sensor on each head, the sound conduction can be turned off when a sensor head 10 is rotated away from the patient by a suitable design of the couplings 4.

Figure 6:
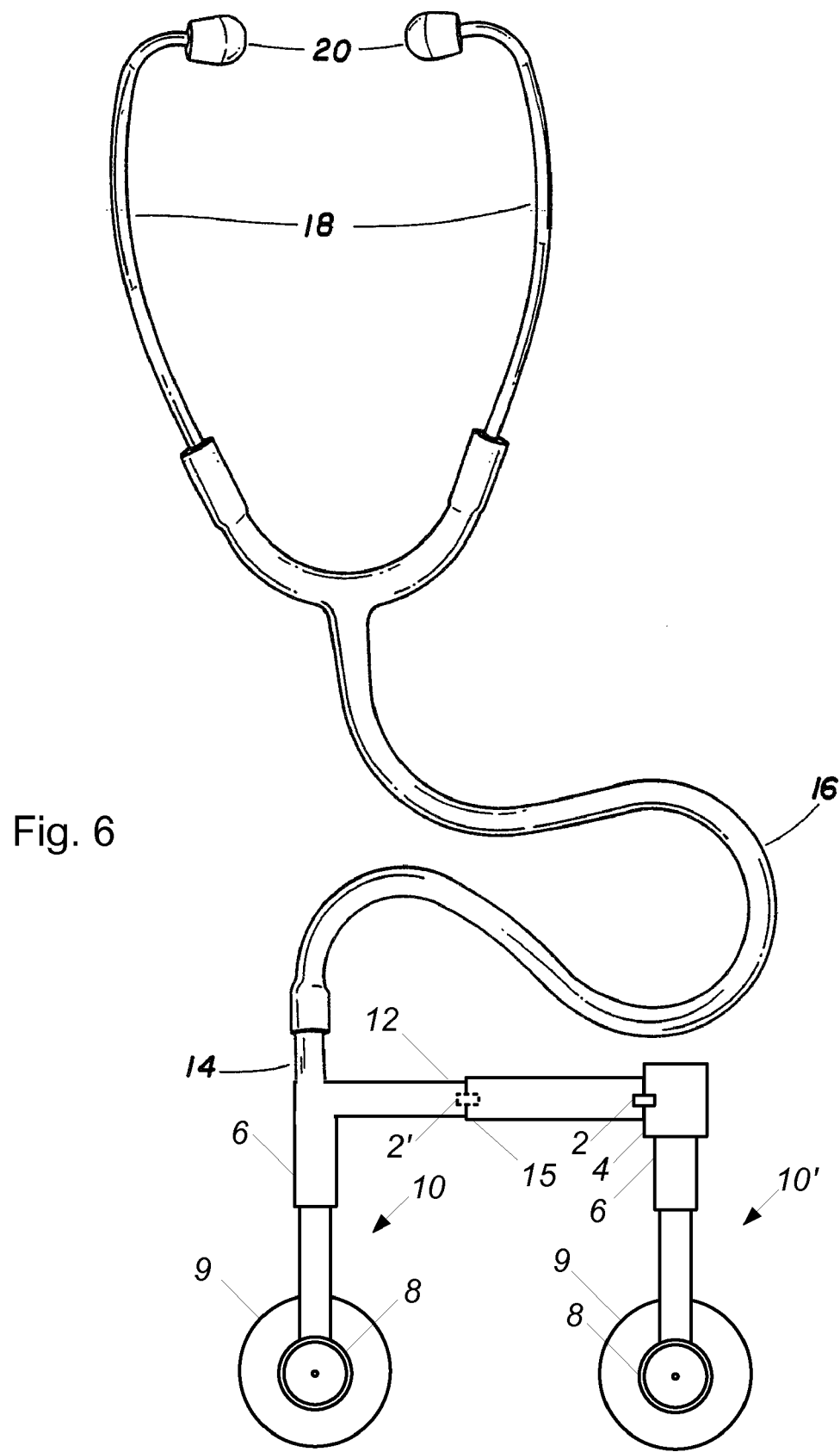
FIG. 6 illustrates an embodiment that has only one rotatable head.

While there is no overriding need to position the sensor head 10' that has been rotated away in a rigid fashion since the clinician will not be exerting any force on the unused head, it still may be preferable to use a detent or locking means 2 to retain the unused sensor head in a predetermined position away from the patient, such as the illustrated 90° position. While it may be preferable to allow both sensor heads 10 to be rotated, it is also possible to use an embodiment in which only one head 10' is rotatable to another position, as illustrated in FIG. 6.

The device can be made of any material suitable for use in a medical environment that has the desired mechanical and acoustic properties, including but not limited to stainless steel, silver, silver-plated metals, rubber, silicone, PVC, polypropylene, polyethylene, ABS, SAN, polycarbonate, polystyrene, polyester and combinations thereof. To further the anti-septic function of the device, the materials can also have or be treated to have anti-microbial properties, as is known in the art.

In the illustrated embodiments of FIGS. 1-3, the longitudinal dimension of the tube 12 determines the separation distance of the sensors 10. In use, this dimension can be determined based upon the desired separation distance of the sensors for either stereoscopy or alternate auscultation between the two sensors. A clinician can have variously sized devices or tubes 12 to select from, dependant on the desired application, with either the entire T-shaped support or parts thereof being replaceable for different applications. For example, devices for pediatric use will typically be of smaller dimensions.

Figure 4:
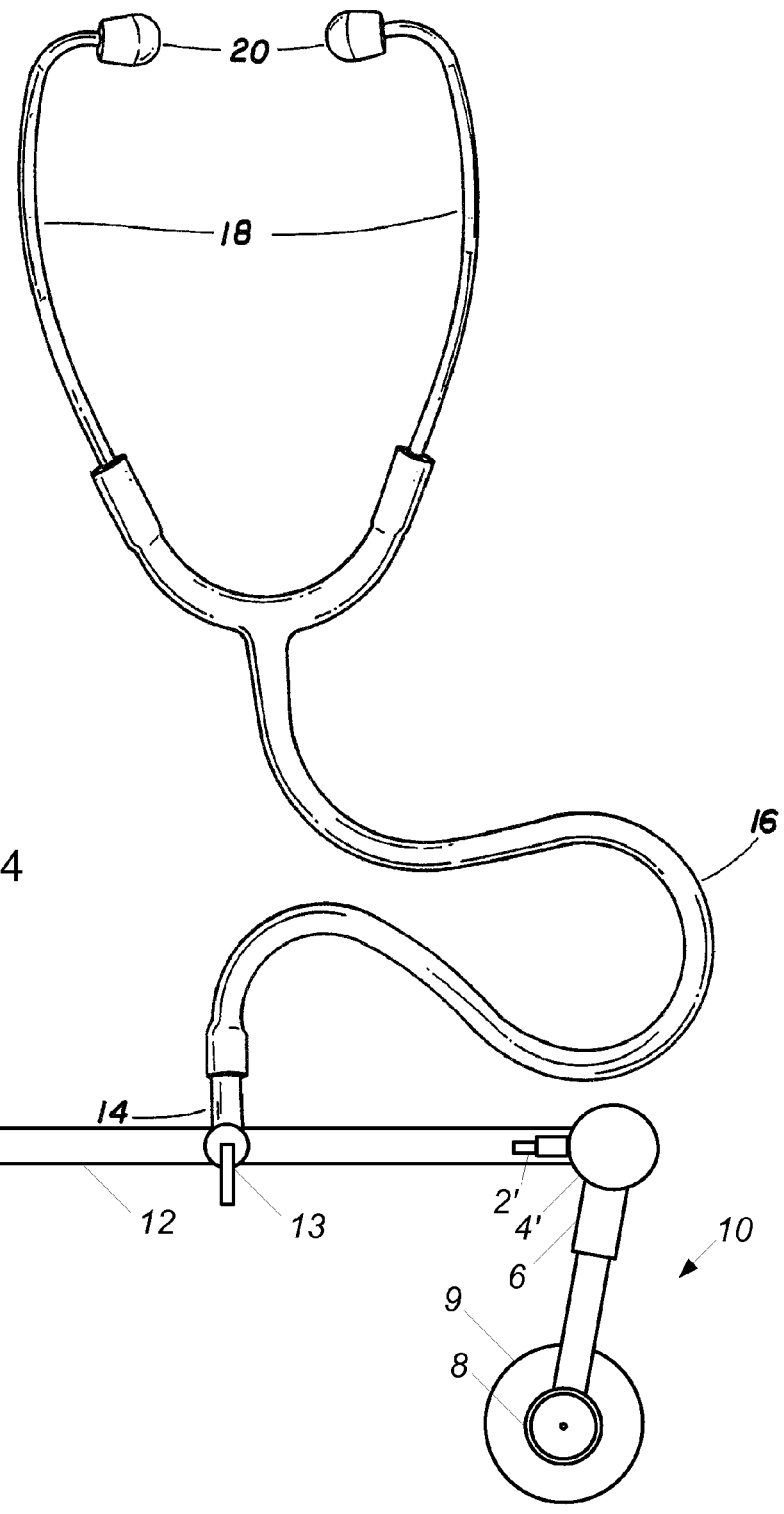
FIG. 4 illustrates an embodiment utilizing a ball pivot.
Figure 5:
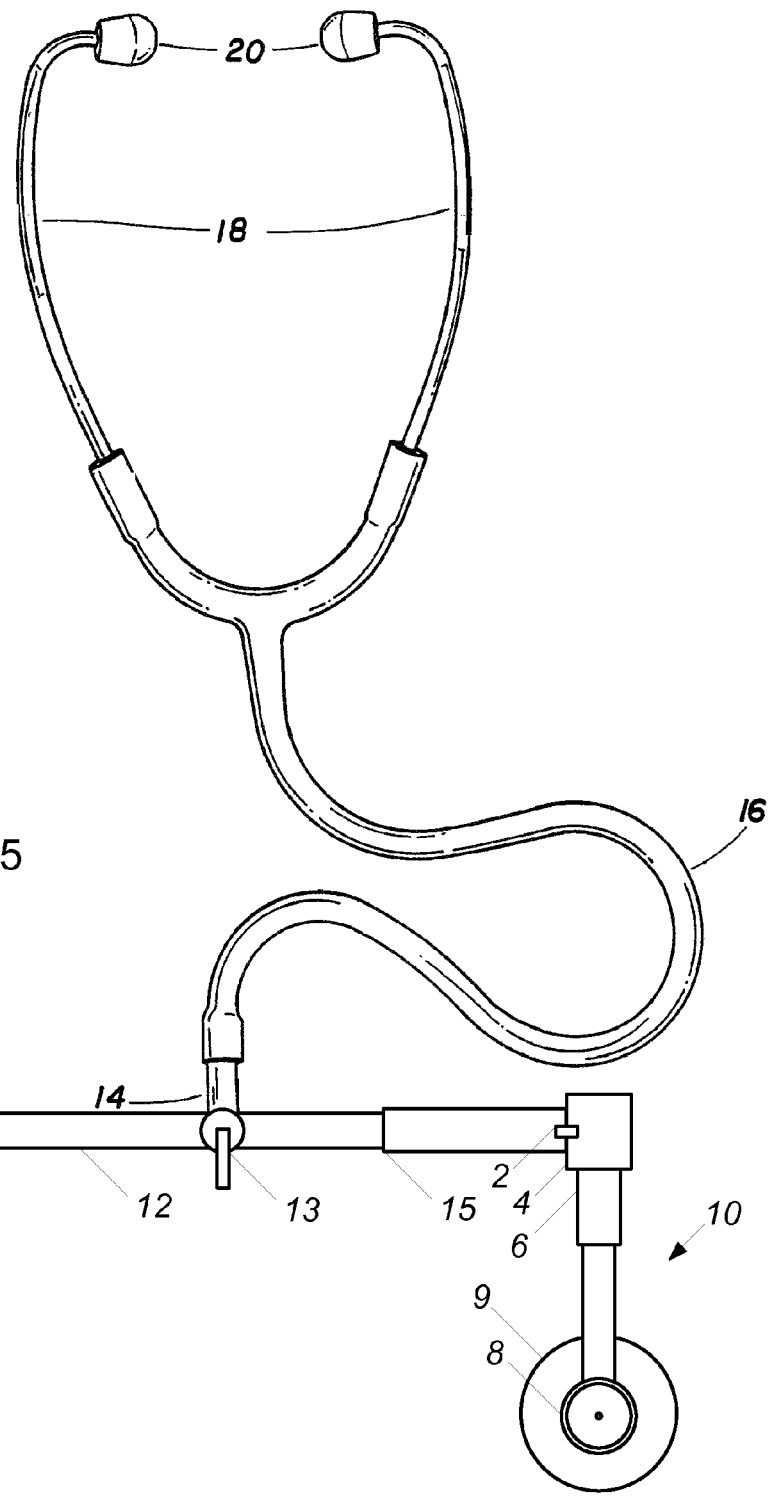
FIG. 5 illustrates an embodiment utilizing a telescoping element.

Alternately, various other means can be used for varying the distance between the sensors 10. As illustrated in FIG. 4, one or both (not shown) of couplings 4 can be a multi-directional or ball pivot 4' so as to be able to vary the distance between the sensors. A frictional lock 2' can be used to maintain the position of the sensor 10. Alternately, a re-positional flexible tube could also be used, but would be more difficult to keep in position. As illustrated in FIG. 5, a telescoping element 15 can also be used to vary the distance between the two sensors.

As illustrated in FIG. 6, an embodiment can employ only a single rotatable head 10' for purposes of simplicity. While illustrated as having a telescoping element 15, such an element is not required. However, if the telescoping element 15 is integrated with the rotatable coupling 4, the overlapping portions between tube 12 and element 15 can be used as a bearing for the coupling, with the detent or lock 2' moved to the end of element 15. While only a single telescoping element 15 is illustrated, multiple elements can be used to further expand the range of the sensor separation distance.

As illustrated in FIGS. 1-6, typical stethoscope bells, heads or sensors 10 include a rigid extension tube that would ordinarily be inserted into the flexible sound conduction tube 16 of a stethoscope, but in the illustrated embodiments are inserted into tubes 6, which are dimensioned to accommodate the intended sensor 10. As such, tubes 6 can be dimensions for the rigid extension tubes of either standard adult or pediatric stethoscope heads. FIG. 7 illustrates an alternate embodiment in which the rigid extension tube is formed to integrally attach to tube 12, such as might be done for disposable sensors manufactured for use with in the invention.

Figure 8:
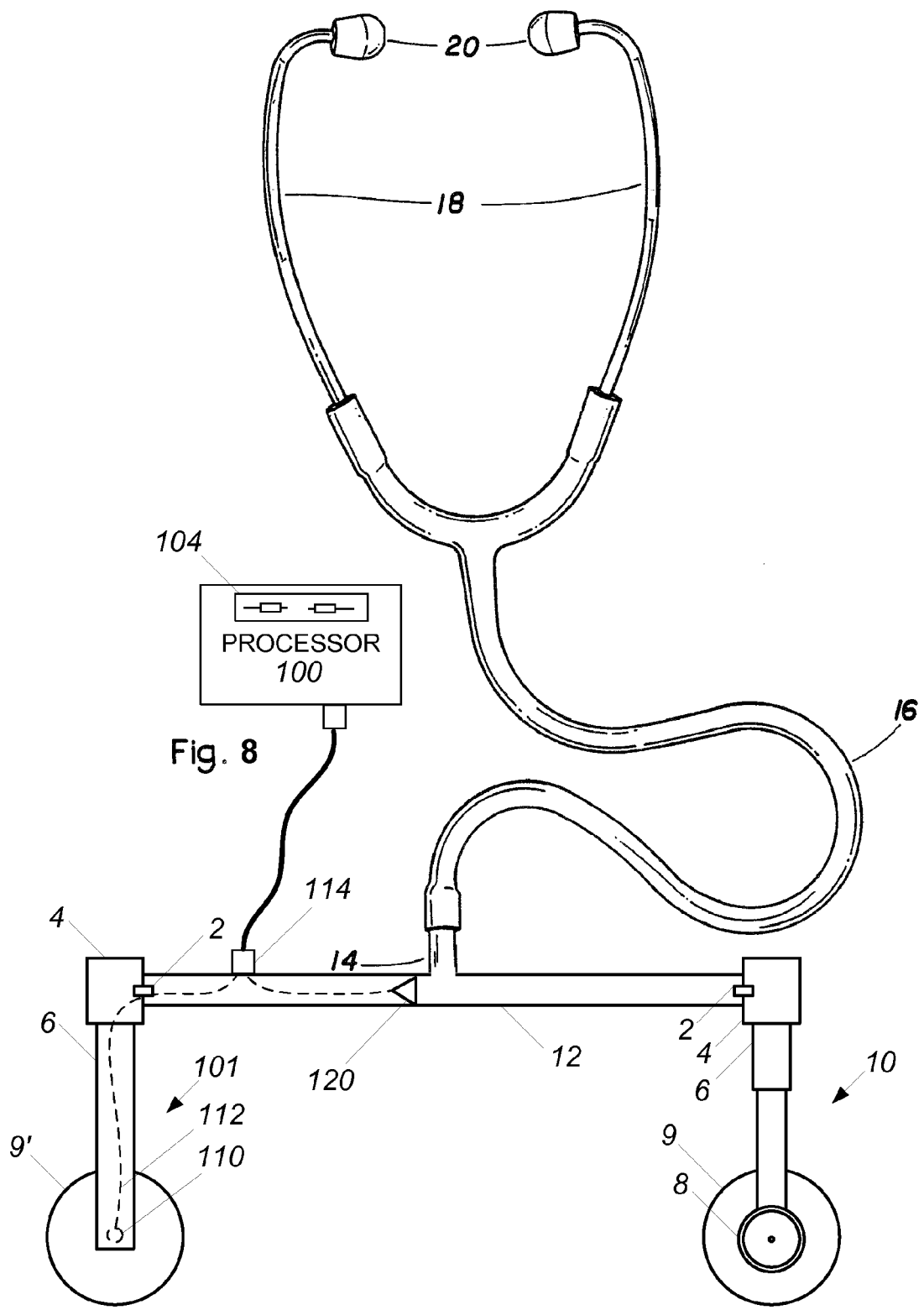
FIG. 8 illustrates an embodiment with a single electronic sensor.

FIGS. 8-10 illustrate embodiments that incorporate at least one electronic sensor. While similar in configuration to the configuration illustrated in FIG. 1, with identical reference numbers for identical elements, the tube adjustment means for controlling or varying the distance between the dual sensors as illustrated in FIGS. 4-7 can also be incorporated into the embodiments of FIGS. 8-10. The embodiments of FIGS. 8-10 retain all of the anti-sepsis functionality and constructive interference functionality as described above, but benefits further from the processing capabilities made possible by use of electronic sensor elements. Further, although the electronic signals are shown as being transported by wires, this is not meant as a limitation and wireless (e.g., RF) links can be used wherever wired connections are illustrated.

As illustrated in FIG. 8, an embodiment of a stethoscope includes conventional eartips 20 and earpieces 18 connected to common sound conduction tube 16. In place of a conventional stethoscope head at the end of the tube 16, a substantially rigid structure is used to mount two sensors 101, 10 to the stethoscope, wherein sensor 101 is electronic and sensor 10 is mechanical. In use, a clinician can handle the rigid structure to position the sensors 101, 10 and thus avoid contamination of the sensors 101, 10 from any pathogens that may be on the clinician's hands. In the illustrated configuration of FIG. 8, the stethoscope is configured in a position for stereoscopy wherein the stethoscope sensors 101, 10 will transmit sound through common sound conduction tube 16, which results in constructive interference of sound waves.

The electronic sensor 101 includes a sound collection element 9' corresponding generally to a mechanical diaphragm, a microphone element 110, wiring 112, and connections 114 as needed. Signals from microphone 110 are transmitted to a processor 100 and the processed output is sent to an audio output 120, such as a speaker, to produce sound waves for conduction to the common sound conduction tube 16. While illustrated in tube 12, the audio output 120 can also be located in sensor-support tube 6. Controls 104 can be provided on the processor, such as sliders (illustrated), dials, or buttons to control volume, frequency range, etc. of the audio output at 120.

Again, the generally T-shaped support tube includes a first tubular element 14 sized for connecting to common sound conduction tube 16. When used with conventional stethoscopes, the element 14 will be a tube having the same dimensions as the connection tube of a conventional sensor head. Similarly, when used with pediatric stethoscopes, the element 14 will be a tube having the same dimensions as the connection tube of a pediatric sensor head or can alternately include an adapter element (not shown) to allow connection to a pediatric stethoscope.

The T-shaped support tube further includes tube 12 that communicates with element 14 in a central portion and with two rotatable sensor-supporting tubes 6 at first and second spaced ends of tube 12. Sensor-supporting tubes 6, when used with conventional stethoscope sensors, are dimensioned to allow insertion and connection of conventional sensor heads 10 with bells 8 and/or diaphragms 9, whether regular and pediatric. Tubes 6 are rotatably attached to tube 12 with rotatable couplings 4 that can be integral or separate from tubes 6. The rotatable coupling 4 preferably includes or cooperates with a detent or locking means 2 so as to form a substantially rigid support for the sensors 101, 10 that the clinician can grasp and use for obtaining the desired seal or contact of the sensor 101 and/or 10 against the patient.

Although the length of tube 12 is illustrated to show a clear distance between the sensor heads 101, 10, in some embodiments it may be preferable to minimize the length of tube 12 (e.g., only slightly longer than the diameter of each sensor head) in order to allow a clinician to manipulate both sensor heads 10 with a single hand, as illustrated in FIG. 7. Additionally, although tubes 6 are illustrated as being identical, the tubes 6 can also have different lengths or have different diameters to allow the use of variously-sized sensors (e.g., a full-sized sensor and a pediatric sensor) on the same stethoscope. Further, an embodiment may comprise only elements 2, 4, 6, 101, 10, 120, 12, and 14 as a separate unit to retro-fit to existing stethoscopes.

In use, the processor 100 and controls 104 can be used to vary the volume, frequency range, etc. of the contribution from electronic sensor 101 without requiring the clinician to vary the placement of the sensors 101, 10.

In the embodiment illustrated in FIG. 9, both sensors 101 are electronic and can be processed by the processor 100 to provide audio output at 120. With both sensors 101 capable of being processed, the use of a balance control or separate volume controls on controls 104 allows the contribution from each sensor 101 to be adjusted independently so a to provide the basic functionality of the "binary" stopcock of FIGS. 3-5 as well as variations not possible with such a binary system. Additionally, processing of other variables such as the frequency band allows functionality not available from typical mechanical stethoscopes.

FIG. 10 illustrates a completely electronic embodiment in which signals from sensors 101 are sent to processor 100 and the processed output sent to a connector on the processor for connection to earphones 130 worn by the clinician (illustrated) or other external audio device such as a speaker (not shown). Earphones 130 or other output can be operated in mono for constructive interference or in stereo for directional listening. This embodiment retains the functionality of the embodiment of FIG. 9, but eliminates the sound losses from common conduction tube 16, earpieces 18 and eartips 20. In such an embodiment, it may be beneficial to optionally provide a handle 118 for easier handling by the clinician. When used, the handle 118 along with the processor and/or the earphones 130 can be reusable, with the remaining elements disposable to further promote anti-sepsis. Further, although not illustrated, the processor 100 can be integrated more into the handle 118 and the handle 118 can optionally have angle adjustment means for better ergonomics.

Embodiments of the invention can be incorporated into a complete dual-head antisepsis stethoscope or as a device to convert an ordinary stethoscope into dual-head antisepsis stethoscope. Either type of embodiment can include a connection tube dimensioned to engage a sound conduction tube of the stethoscope; a second tube connected to the connection tube, the second tube having a first end and a second end; a first sensor head-supporting tube coupled to the first end of the second tube; and a second sensor head-supporting tube coupled to the second end of the second tube; wherein at least one of the first and second sensor head-supporting tubes is rotatably coupled relative to the second tube.

Further embodiments can optionally include various details, including but not limited to one or more of: having both the first and second sensor head-supporting tubes are rotatably coupled relative to the second tube; having a detent or locking means for restraining movement of the at least one sensor head-supporting tube that is rotatably coupled relative to the second tube; having a stethoscope head integrated into each of the first and second sensor head-supporting tubes; having the device or parts thereof constructed from disposable materials; having the second tube further comprise at least one telescoping element; having the second tube connected to the connection tube at a location between the first and second ends; having a three-way stopcock positioned at the location between the first and second ends where the second tube is connected to the connection tube; and having the connection tube directly connected to one of the first and second sensor head-supporting tubes.

A device for providing a dual-sensor anti-sepsis stethoscope with at least one electronic sensor has been described. It will be understood by those skilled in the art that the present invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular.

What is claimed is:

1. A dual-head anti-sepsis stethoscope device comprising:
   a connection tube dimensioned to engage a sound conduction tube of a stethoscope;
   a second tube connected to the connection tube, the second tube having a first end and a second end;
   a first sensor head-supporting tube coupled to the first end of the second tube;
   a second sensor head-supporting tube coupled to the second end of the second tube; wherein at least one of the first and second sensor head-supporting tubes is rotatably coupled relative to the second tube;
   an electronic sensor incorporating a microphone attached to the first sensor head-supporting tubes at an end opposite the second tube;
   a processor for processing signals from the microphone to produce processed audio signals; and
   an audio output means for receiving the processed audio signals, wherein said audio output means is positioned in one of the locations selected from the group consisting of the connection tube, the second tube, and the first sensor head-supporting tube.

2. The dual-head anti-sepsis stethoscope device of claim 1, wherein the first and second sensor head-supporting tubes are rotatably coupled relative to the second tube.

3. The dual-head anti-sepsis stethoscope device of claim 1, further comprising:
   a detent or locking means for restraining movement of the at least one sensor head-supporting tube that is rotatably coupled relative to the second tube.

4. The dual-head anti-sepsis stethoscope device of claim 1, further comprising:
   a second electronic sensor comprising a second microphone and attached to the second sensor head-supporting tubes at an end opposite the second tube;
   the processor further processing signals from the second microphone to produce the processed audio signals; and
   the audio output means positioned in the connection tube.

5. The dual-head anti-sepsis stethoscope device of claim 1, wherein portions of the device other than the processor are constructed from disposable materials.

6. The dual-head anti-sepsis stethoscope device of claim 1, wherein the processor comprises manually operated controls.

7. The dual-head anti-sepsis stethoscope device of claim 1, wherein the second tube further comprises at least one telescoping element.

8. The dual-head anti-sepsis stethoscope device of claim 1, wherein the second tube is connected to the connection tube at a location between the first and second ends.

9. The dual-head anti-sepsis stethoscope device of claim 4, wherein the processor comprises separate manually operated controls for each electronic sensor.

10. The dual-head anti-sepsis stethoscope device of claim 1, wherein the connection tube is directly connected to one of the first and second sensor head-supporting tubes.

11. A dual-head anti-sepsis stethoscope, comprising:
    an eartip;
    an earpiece attached to the eartip;
    a common sound conduction tube attached to the earpiece;
    a connection tube dimensioned to engage the common sound conduction tube at an end opposite an end attached to the earpiece;
    a second tube connected to the connection tube, the second tube having a first end and a second end;
    a first sensor head-supporting tube coupled at a first end to the first end of the second tube;
    a first sensor head attached to a second end of the first sensor head-supporting tube;
    a second sensor head-supporting tube coupled at a first end to the second end of the second tube; and
    a second sensor head attached to a second end of the second sensor head-supporting tube;
    wherein at least one of the first and second sensor head-supporting tubes is rotatably coupled relative to the second tube; and
    wherein at least one of the first and second sensor heads is an electronic sensor with a microphone; and further comprising:
    a processor for processing signals from the microphone to produce processed audio signals; and
    an audio output means for receiving the processed audio signals, wherein said audio output means is positioned in one of the locations selected from the group consisting of the connection tube, the second tube, and the sensor head-supporting tube attached to the electronic sensor.

12. A dual-head anti-sepsis stethoscope, comprising:
    a tube having a first end and a second end;
    a first sensor head-supporting tube coupled at a first end to the first end of the tube;
    a first sensor head attached to a second end of the first sensor head-supporting tube;
    a second sensor head-supporting tube coupled at a first end to the second end of the tube; and
    a second sensor head attached to a second end of the second sensor head-supporting tube;
    wherein at least one of the first and second sensor head-supporting tubes is rotatably coupled relative to the second tube; and
    wherein each of the first and second sensor heads is an electronic sensor with a microphone; and further comprising:
    a processor for processing signals from the microphone to produce processed audio signals; and
    an audio output connector from the processor for receiving the processed audio signals.

13. The dual-head anti-sepsis stethoscope device of claim 12, further comprising:
    a detent or locking means for restraining movement of the at least one sensor head-supporting tube that is rotatably coupled relative to the tube.

14. The dual-head anti-sepsis stethoscope of claim 12, wherein both the first and second sensor head-supporting tubes are rotatably coupled relative to the second tube.

15. The dual-head anti-sepsis stethoscope of claim 12, wherein the stethoscope is dimensioned for pediatric use.

16. The dual-head anti-sepsis stethoscope of claim 12, wherein the sensors are constructed from disposable materials.

17. The dual-head anti-sepsis stethoscope of claim 12, wherein the tube further comprises a telescoping element.

18. The dual-head anti-sepsis stethoscope of claim 12, wherein the tube is connected to a handle at a location between the first and second ends.

19. The dual-head anti-sepsis stethoscope of claim 12, wherein the processor comprises separate manually operated controls for each electronic sensor.

20. The dual-head anti-sepsis stethoscope of claim 12, further comprising earphones connected to the audio output connector from the processor.

* * * * *